United States Patent
Diaz

(10) Patent No.: US 6,469,068 B2
(45) Date of Patent: Oct. 22, 2002

(54) COMPOSITION FOR DISINFECTING TOOTHBRUSHES AND OTHER ORAL CAVITY CLEANING INSTRUMENTS

(76) Inventor: Richard Allen Diaz, 14 Branch La., East Setauket, NY (US) 11733

( * ) Notice: Subject to any disclaimer, the term of this patent is extended or adjusted under 35 U.S.C. 154(b) by 0 days.

(21) Appl. No.: 09/896,048

(22) Filed: Jun. 29, 2001

(65) Prior Publication Data

US 2002/0057988 A1 May 16, 2002

Related U.S. Application Data

(63) Continuation of application No. 09/498,209, filed on Feb. 4, 2000, now abandoned.

(51) Int. Cl.[7] ..................... A61K 31/045; A61K 31/05; A61N 31/08
(52) U.S. Cl. ....................................... 514/724; 514/731
(58) Field of Search .................................. 514/724, 731

(56) References Cited

U.S. PATENT DOCUMENTS 5,730,965 A * 3/1998 Rapaport ..................... 424/70
5,990,100 A * 11/1999 Rosenberg et al. ......... 514/174

FOREIGN PATENT DOCUMENTS

WO 9825586 * 6/1998

* cited by examiner

*Primary Examiner*—Alton Pryor
(74) *Attorney, Agent, or Firm*—Ohlandt, Greeley, Ruggiero & Perle, L.L.P.

(57) ABSTRACT

There is provided a composition comprising an alcohol, a surfactant other than a cationic surfactant, and, optionally, a phenolic in active amounts particularly suitable to disinfect toothbrushes and other oral cavity cleaning instruments. The composition may also include an emulsifier. Preferably, the composition comprises an alcohol, a surfactant other than a cationic surfactant, and a phenolic. More preferably, the surfactant is an anionic surfactant.

8 Claims, 1 Drawing Sheet

COMPOSITION FOR DISINFECTING TOOTHBRUSHES AND OTHER ORAL CAVITY CLEANING INSTRUMENTS

This is a continuation, of application Ser. No. 09/498,209, filed on Feb. 4, 2000, now abandoned.

BACKGROUND OF THE INVENTION

1. Field of the Invention

The present invention relates to compositions for controlling germs, such as bacteria, viruses, and mold. More specifically, the present invention relates to compositions for controlling germs that grow on instruments used to clean inside the oral cavity.

2. Description of the Prior Art

Recently, the news media have focused on the microbial dangers one confronts on a daily basis. Food-borne illnesses have received particular attention. In fact, the Centers for Disease Control are beginning a major effort to quantify and limit the increase in food-borne illness. In addition, the role of mold spores as a cause of allergy has been well documented. Recently, *Stachybotrys atra* has received close attention as a potentially dangerous household fungus. Furthermore, advertisements for products for disinfecting or sanitizing surfaces in the home and advertisements for hand sanitizing soaps and lotions can be seen on television during prime time.

Yet, while millions of toothbrushes are sold each year, the average American buys less than one toothbrush per year. Also, there is little public awareness that, with use, toothbrush bristles become heavily contaminated by germs. A toothbrush used in the morning may not be used again until twelve to fourteen hours later, which affords ample opportunity for germ growth. This is of particular concern for the increasing population of elderly and immuno-impaired patients, as well as young children, because oral contaminants constitute an important cause of opportunistic infections. Even in otherwise healthy people, inadequate oral hygiene and dental maintenance has been increasingly linked to disease ideology.

A germ is generally defined herein as any microorganism from which growth and development are expected. This includes viruses, bacteria, mold, fungus, pollen, protozoan, yeast, and algae. Specifically in reference to toothbrushes and other oral cavity cleaning and periodontal instruments, normal microbiota include viridans group streptocci, which are the most common group of microorganisms in the oral cavity and Moraxella catarrhalis. Potential pathogens include *Staphylococcus aureus, Streptococcus pneumoniae, Streptococccus pyogenes, E. coli, Pseudomonas aeruginosa, Neisseria meningitidis, Haemophilus influenzae,* and *Candida albicans* (a fungus), and *Moraxella cararrhalis*. Primary infections, such as scarlet fever, and streptococcal toxic shock syndrome, as well as several dangerous late sequelae, such as rheumatic fever and hemorrhagic glomerulonephritis are caused by *S. pyogenes*.

Millions of germs inhabit the human oral cavity, and many have the capacity to cause sickness and infections. Germs are capable of growing on the minuscule food particles that remain trapped within the bristles of a toothbrush after use. Furthermore, many families store their toothbrushes in a common container in a moist, humid bathroom that facilitates germ growth and cross-contamination. In fact, studies have shown that the bathroom may be the most contaminated room in the home. Pointedly, when individuals brush their teeth with used toothbrushes, they put an implement teeming with dangerous germs into their mouths. It is also likely that the bristles of contaminated toothbrushes play a role in the transmission of contaminating germs by abrading the gums being brushed. Clearly, controlling germs on toothbrushes deserves serious attention.

Germs can be controlled through sterilization. Sterilization refers to the complete destruction of all forms of life including bacterial endospores. Destruction of bacterial endospores is most readily achieved by the use of physical methods, most often moist heat, at temperatures well above the boiling point of water, i.e., autoclaving. Yet, autoclaving is too time, labor, and money intensive for practical domestic use. Additionally, many contaminated items are heat sensitive and, therefore, chemical methods must be used. Chemical sterilization is time consuming and uses agents, such as glutaraldehyde, which are relatively toxic. Therefore, chemical sterilization should not be considered for practical domestic use.

Germs can also be controlled by disinfection. Disinfection refers to the destruction of only those organisms that are either primary causes of infectious disease or act as secondary invaders. The destruction of the most commonly encountered organisms of clinical interest is within the capability of a variety of chemical agents. These organisms include bacteria that are relatively resistant, such as *Mycobacterium tuberculosis* and viruses, such as HIV, herpes, respiratory syncytial, influenza A and B, parainfluenza, coxsackie, rotavirus, and caliciviruses (agent of acute infectious non-bacterial gastroenteritis), as well as the vegetative cells of endospore forming species of both Bacillus species and Clostridium species. Disinfection is clearly more appropriate for toothbrushes and other oral cavity cleaning instruments compared to sterilization.

Chemical disinfection is affected by the nature and concentration of the chemical, and the amount of time the germ is exposed to the chemical. For instance, merely dipping a toothbrush into a small container of a disinfectant will obviously be less effective than soaking the toothbrush over-night. Other factors affecting chemical disinfection include the presence or absence of organic or inorganic material as well as pH and temperature. The presence of protein on the surface of the item to be disinfected may inactivate the disinfectant and protect the microorganisms. The surface of the item to be disinfected must also be taken into account. For example, hard smooth surfaces are more readily disinfected than soft porous surfaces.

There are several tried and true classes of disinfectants, each with their own advantages and disadvantages.

Phenolics, such as phenol, have been used as anti-germ ingredients. Yet, phenol is less frequently used today. Phenolics have a chemically altered phenol molecule, which reduces toxicity and enhances antibacterial activity. The most well known phenolics are cresols, known by the names Lysol, O-Syl, and Amphyl, which are used as environmental disinfectants. The bis-phenols, such as hexachlorophene, enjoyed popularity for many years, but now require a prescription. Phenolics coagulate protein and, when combined with surfactants, are also virucidal, fungicidal and tuberculocidal, but are not sporicidal agents.

Alcohols, in a concentration of 50 percent to 80 percent of the total weight of the composition, are lethal for *M. tuberculosis* and the vegetative forms of other bacteria as well as enveloped viruses. Alcohols have a broad spectrum of virucidal activity, demonstrating effectiveness against lipophilic viruses (adenovirus, herpes, and influenza) as well as hydrophilic viruses (poliovirus 1, echovirus 6, coxsackie B1). Yet, alcohol cannot combat non-enveloped viruses. High proof alcohols also have a distinctive, and often unpleasantly strong, taste and aroma. Such an obnoxious taste and aroma is clearly undesirable in a composition for disinfecting toothbrushes.

Surface active agents, such as detergents, exert their antimicrobial action by wetting the surface of the microbe. In other words, surface active agents form a bridge between the interior contents of the cell and the external environment. This often causes the cell to become denatured, which results in cell injury or death. Cationic detergents, a subclass of surface active agents, form positively charged ions causing adherence to microorganisms. This group includes the quaternary ammonium compounds. These compounds are limited by their affinity for many proteins and for soaps. They are readily bound and inactivated by plant fibers. Although effective against some gram-positive organisms, they are relatively ineffective against gram negative organisms. *Pseudomonas aeruginosa* has been found to utilize some quaternary ammonium compounds as a substrate for growth.

Oxidizing agents, such as iodine, chlorine, bromine, and fluorine, combine irreversibly with protein, inhibiting enzyme activity within bacteria. For example, a 1:10 dilution of household bleach (containing 0.5% sodium hypochlorite) is recommended by the Centers for Disease Control as an effective and inexpensive disinfectant. As another example, iodophores (iodine complexed with organic molecules) are common nonionic detergents and are used for disinfection. Glutaraldehyde and formaldehyde are highly effective. However, oxidizing agents can be toxic, and are often bleaching, corrosive, and malodorous.

Some prior art disinfectants contain alcohol combined with a dilute phenolic, which enhances the disinfecting activity of the alcohol and also inhibits non-enveloped viruses.

However, this formulation, which is typical for mouthwashes, such as Listerine™, and other popular products of a similar nature, may not be effective as a toothbrush cleaner. The main reason is because mouthwashes are taken into the oral cavity in considerable amounts. Thus, some effective germ-controlling ingredients and combinations are removed if they have a disagreeable taste or smell. Furthermore, reasonably conservative safety proscriptions are necessary due to the delicate nature of the mucous membrane within the oral cavity. Thus, many effective germ-controlling ingredients cannot be used directly on the teeth and gums.

In light of the prior art, there is a need for a combination of germ controlling ingredients specifically intended to clean and disinfect a toothbrush.

SUMMARY OF THE INVENTION

It is an object of the present invention to provide a disinfecting composition.

It is another object of the present invention to provide such a disinfecting composition for use with toothbrushes and other oral cavity cleaning instruments.

It is still another object of the present invention to provide such a disinfecting composition for use with toothbrushes and other oral cavity cleaning instruments that is both effective against germs and safe for consumers to use.

Accordingly, the present invention provides a composition comprising an alcohol, a surfactant other than a cationic surfactant, and, optionally, a phenolic in active amounts particularly suitable to disinfect toothbrushes and other oral cavity cleaning instruments. The composition may also include an emulsifier. Preferably, the composition comprises an alcohol, a surfactant other than a cationic surfactant, and a phenolic. More preferably, the surfactant is an anionic surfactant.

DETAILED DESCRIPTION OF THE INVENTION

Figure 1:
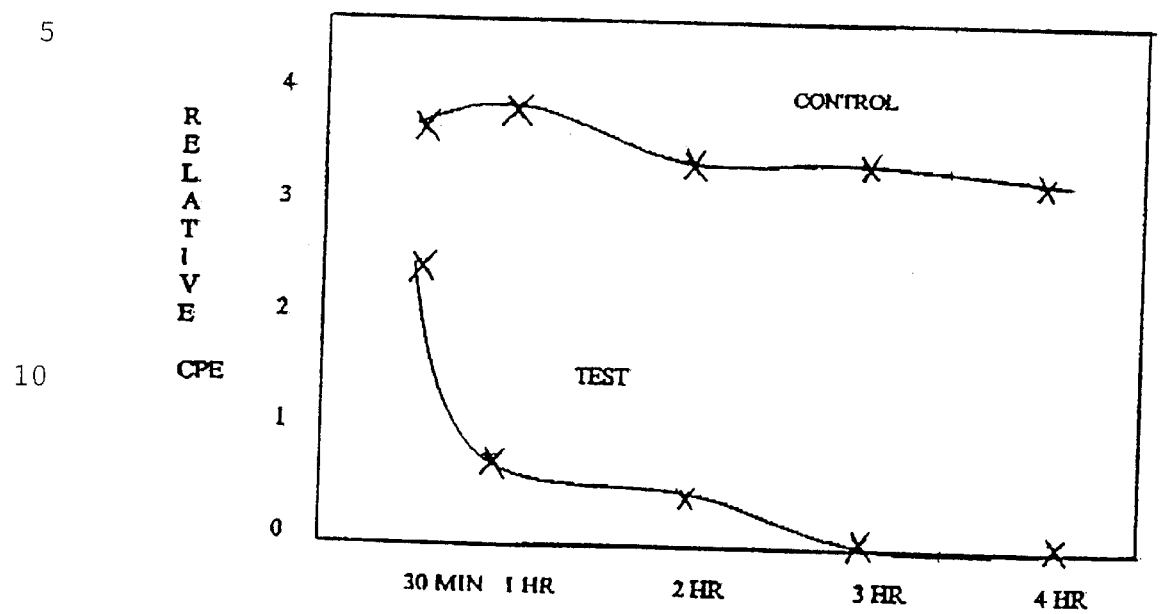
FIG. 1 Disinfecting solution with PCMX against enterovirus.

The present invention provides a germ controlling composition comprising an alcohol, a surfactant other than a cationic surfactant, and, optionally, a phenolic. The composition may also include an emulsifier. The relative percentages of these ingredients within the total composition are set to promote the disinfection of toothbrushes and other oral cavity cleaning and periodontal instruments, such as gum stimulators, tongue scrapers, and plaque removers.

Alcohol is used in the present invention for controlling bacteria, such as *M. tuberculosis* and the vegetative forms of other bacteria, and destroying enveloped viruses, as well as lipophilic and hydrophilic viruses. Alcohols useful in the present invention include ethanol, propanol, and isopropanol. Ethanol is particularly useful in the present invention. The preferred concentration of alcohol is about 40 percent by weight (wt %) to about 80 wt % of the total weight of the composition. Below about 40 wt %, alcohol is not as effective against enveloped viruses. At concentrations below about 50 wt %, alcohol is not as effective a disinfectant. Since the effect of alcohol depends on the presence of water, alcohol becomes less effective at concentrations above about 80 wt %. The more preferred range of alcohol is about 50 wt % to about 70 wt %, with 50 wt % being the most preferred concentration.

The present composition also includes a surfactant other than a cationic surfactant. The surfactant, which may be nonionic or anionic, is used to solubilize proteins and aid in removing saliva, buccal mucosal cells, blood, plaque, and food particles from the oral cavity cleaning instrument.

The surfactant is preferably an anionic surfactant. Anionic surfactants have strong detergent qualities. Anionic surfactants also exhibit antibacterial activity and have a greater ability to bind to proteins. Furthermore, it has been determined that a synergistic effect exists between anionic surfactants and phenolic compounds.

A particularly useful anionic surfactant is sodium lauryl sulfate, which is also known as sodium dodecyl sulfate. Sodium lauryl sulfate generally conforms to the following formula:

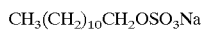

Preferably, the nonionic or anionic surfactant is present in an amount about 0.025 wt % to about 1 wt % of the total weight of the composition. Below about 0.025 wt %, the efficacy of the nonionic or anionic surfactant decreases. Above about 1 wt %, the nonionic or anionic surfactant will not necessarily guarantee better results. More preferably, the non-cationic surfactant is present is an amount about 0.075 wt % to about 0.5 wt % and, most preferably, about 0.2 wt %.

In one embodiment of the present invention, the composition includes an alcohol and a surfactant other than a cationic surfactant, preferably in the preferred amounts. In a more preferred embodiment, the composition includes an alcohol, a nonionic or anionic surfactant, and phenol or a phenolic ingredient.

One of the primary purposes of the phenolic ingredient is to control non-enveloped viruses. The phenolic ingredient may be present in an amount about 0.025 percent by weight to about 9 wt % of the total weight of the composition. The phenolic ingredient may more preferably be present in an amount about 0.075 wt % to about 0.5 wt %, and most preferably about 0.1 wt % to about 0.2 wt %.

A phenolic useful in the present invention is phenol, which conforms to the following general formula:

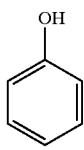

When used, phenol is preferably present in the range from about 0.025 wt % to about 5 wt % of the total weight of the composition. Below about 0.025 wt % its effectiveness as a disinfectant decreases and toxicity becomes a concern at above about 5 wt %. More preferably, the phenol is present in an amount about 0.075 wt % to about 0.25 wt %, and most preferably about 0.1 wt %. At ranges above about 0.25 wt %, odor could start to become an issue, as well as clouding of certain plastics. At less than about 0.1 wt %, phenol is not as effective in performing its function.

Other useful phenolic ingredients include halogenated phenolics. A preferred halogenated phenolic is 4-chloro-3,5-dimethyl phenol. 4-chloro-3,5-dimethyl phenol is particularly effective against enterovirus, a common respiratory virus. 4-chloro-3,5-dimethyl phenol is herein referred to as PCMX. The structural formula of PCMX is:

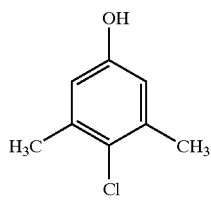

When used, the preferred amount of PCMX is about 0.025 wt % to about 4 wt % of the total weight of the composition. Below about 0.025 wt % its effectiveness as a disinfectant decreases. Above about 4 wt % the question of toxicity becomes a concern. The more preferred amount is about 0.075 wt % to about 0.25 wt %. The most preferred concentration or amount is about 0.1 wt %. At ranges above about 0.25 wt %, odor could start to become an issue, as well as clouding of certain plastics. At less than about 0.1 wt %, PCMX is not as effective in performing its function.

The more preferred phenolic ingredient is a combination of phenol and PCMX. When used together, the preferred amount of phenol is preferably about 0.025 wt % to about 5 wt %, while the preferred amount of PCMX is about 0.025 wt % to about 4 wt %.

One or more emulsifiers may also be used in the present invention. The emulsifier assists in dispersing clumps of bacteria, which increases the amount of bacteria exposed to antibacterial ingredients used in the present invention.

A preferred emulsifier for use in the present invention is polysorbate 80. Polysorbate 80 is a mixture of oleate esters of sorbitol and sorbitol anhydrides, having predominantly of monoesters, condensed with approximately 20 moles of ethylene oxide. Polysorbate 80 conforms generally to the following formula:

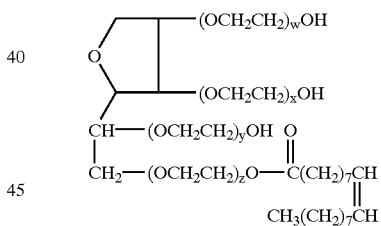

wherein w+x+y+z has an average value of 20.

Preferably, an emulsifier is present in an amount about 0.025 wt % to about 1 wt % of the total weight of the composition. Below about 0.025 wt %, its efficacy in performing its function decreases. A concentration or amount above about 1 wt % will not necessarily guarantee better results. The more preferred range is about 0.075 wt % to about 0.25 wt %, with the most preferred amount being about 0.1 wt %.

A composition according to the present invention may also include other ingredients known to the art, such as water, one or more pH adjusters (i.e. sodium phosphate and sodium phosphite), fragrances, dyes, and artificial or natural favors. These ingredients are provided in amounts appropriate for use in a composition for disinfecting toothbrushes and other oral cavity cleaning and periodontal instruments.

In use, a composition according to the present invention would preferably be used to soak toothbrushes and other oral cleaning instruments. The toothbrushes and other oral cleaning instruments would preferably be immersed in the composition at all times between use. However, the composition would preferably be formulated to effective combat germs even with only a short exposure time.

The following tables summarize the results of experiments that tested two disinfecting solutions against viruses commonly encountered in the respiratory tract. The first solution contained phenol, alcohol, and an anionic surfactant in concentrations according to the present invention. However, the first solution lacked PCMX. The second solution contained PCMX, as well as phenol, alcohol, and an anionic surfactant. The concentrations of all four ingredients in the second solution were set according to the present invention. The viruses used were: Herpes simplex, Respiratory Syncytial Virus (RSV), Influenza A virus, and Enterovirus. The test procedure with both solutions was as follows:

1. Contaminate a control toothbrush and a test toothbrush with the virus to be tested using a suspension of the test virus to a density of about $10^6$ plaque forming units per milliliter.
2. Soak the test toothbrush in the disinfectant solution to be tested for 30 minutes.
3. Elute both test and control toothbrushes in 10 milliliters of sterile culture maintenance medium.
4. Inoculate cell lines with resulting eluate and incubate at 35° C. for 1 to 2 weeks, observing daily for cytopathic effect to determine viral survival or sterility.

TABLE 1

DISINFECTING SOLUTION WITHOUT PCMX

| VIRUS | Relative Number of Cytopathic Effect (CPE) on Test Toothbrush | CPE of Control Toothbrush |
|---|---|---|
| Influenza A | 0 | 3+ |
| RSV | 0 | 3+ |
| Herpes | 0 | 3+ |
| Enterovirus | 3+ | 3+ |

The foregoing results illustrate that significant reduction of Herpes simplex, RSV, and Influenza A virus was demonstrated after the test toothbrushes were soaked for 30 minutes in the first disinfecting solution, which lacked PCMX. However, there was no reduction of enterovirus.

The foregoing results also illustrate that significant reduction of enterovirus was demonstrated after the test toothbrushes were soaked for 30 minutes in the second disinfecting solution, which contained PCMX. Additional testing demonstrated that enterovirus was completely eliminated after the test toothbrushes were soaked for 3 hours in the disinfecting solution having PCMX. These results suggest that PCMX enhances the effectiveness of the present invention against enterovirus.

The following is an example of a disinfecting composition according to the present invention.

EXAMPLE 1

SOLUTION FOR DISINFECTING A TOOTHBRUSH

| Ingredient | Amount |
|---|---|
| 99% ethanol | 500 milliliters |
| phenol | 1 gram |
| Polysorbate 80 | 1 milliliter |
| PCMX | 1 gram |
| sodium lauryl sulfate | 2 milliliters |
| sodium phosphate | 0.56 grams |
| sodium phosphite | 0.37 grams |
| water to 1 liter | |

The present invention having been described with particular reference to the preferred forms thereof, it will be obvious that various changes and modifications may be made herein without departing from the spirit and scope of the invention as defined in the appended claims.

Wherefore we claim:

1. A method for disinfecting an instrument used in the oral cavity comprising the step of contacting said instrument with a composition consisting essentially of an alcohol selected from the group consisting of ethanol, propanol, isopropanol, and mixtures thereof, a surfactant other than a cationic surfactant, a phenolic selected from the group consisting of phenol, 4-chloro-3,5-dimethyl phenol, and mixtures thereof, and optionally an emulsifier.

2. The method of claim 1, wherein said alcohol is present in an amount of about 40 wt % to about 80 wt %.

3. The method of claim 1, wherein said surfactant is present in an amount of about 0.025 wt % to about 1 wt %.

4. The method of claim 1, wherein said surfactant is an anionic surfactant.

5. The method of claim 4, wherein said anionic surfactant is sodium lauryl sulfate.

6. The method of claim 1, wherein said phenolic is present in an amount of 0.025 wt % to about 9 wt %.

7. The method of claim 1, wherein said emulsifier is present in an amount of about 0.025 wt % to about 1 wt %.

8. The method of claim 1, wherein said emulsifier is polysorbate 80.

* * * * *